(12) United States Patent
Pickett

(10) Patent No.: US 7,435,867 B1
(45) Date of Patent: Oct. 14, 2008

(54) TOILET TRAINING KIT AND METHOD FOR TOILET TRAINING

(76) Inventor: Crystal L. Pickett, 3625 E. Ray Rd., Apt. 1011, Phoenix, AZ (US) 85044

( * ) Notice: Subject to any disclaimer, the term of this patent is extended or adjusted under 35 U.S.C. 154(b) by 0 days.

(21) Appl. No.: 11/252,470

(22) Filed: Oct. 17, 2005

Related U.S. Application Data

(60) Provisional application No. 60/701,699, filed on Jul. 22, 2005.

(51) Int. Cl.
*A61F 13/15* (2006.01)
*A61F 13/20* (2006.01)

(52) U.S. Cl. .................. 604/367; 604/361; 206/438

(58) Field of Classification Search ......... 604/361–362, 604/364, 367, 385.01; 434/238; 206/223, 206/438, 581; 119/171–174; 47/9
See application file for complete search history.

(56) References Cited

U.S. PATENT DOCUMENTS

| | | | |
|---|---|---|---|
| 3,921,581 A * | 11/1975 | Brewer | ................. 119/173 |
| 5,649,914 A * | 7/1997 | Glaug et al. | ............. 604/361 |
| 5,725,382 A | 3/1998 | Walter et al. | |
| 5,829,073 A | 11/1998 | Lee | |
| 5,970,916 A * | 10/1999 | Yoder et al. | ................. 119/173 |
| 6,041,737 A * | 3/2000 | Hennigan | ................. 119/165 |
| 6,648,650 B1 | 11/2003 | Fiorella | |
| 6,772,454 B1 | 8/2004 | Barry et al. | |
| 6,908,392 B2 | 6/2005 | Friedman et al. | |
| 2004/0176987 A1* | 9/2004 | Dial et al. | ................. 705/4 |

OTHER PUBLICATIONS

"Potty Training Concepts: Toilet Targets for Boys or Girls" http://www.pottytrainingconcepts.com/Toilet-Targets-Boys-Girls-z.html, Oct. 6, 2005.

* cited by examiner

*Primary Examiner*—Michele Kidwell
(74) *Attorney, Agent, or Firm*—Lowell W. Gresham; Jordan M. Meschkow; Charlene R. Jacobson

(57) ABSTRACT

A toilet training kit (20) includes a case (22) and a plurality of urine indicators (34) housed in the case (22). The kit (20) can also include a mixture (36) of a sugar with a color additive powder dispersed therein. Portions of the urine indicators (34) and the mixture (36) are stored in a plurality of single-use packets (26). Prior to a potty training episode, an entire content of one of the packets (26) is placed in a dry training toilet (38), and the child is positioned on the toilet (38). Urine (42) produced by the child causes the urine indicators (34) to expand and the mixture (36) to dissolve and change the color of the urine to a vivid color, thereby providing amusement to the child. The child's toilet training progress is recorded on a learning graphic (28) provided in the kit (20).

15 Claims, 2 Drawing Sheets

TOILET TRAINING KIT AND METHOD FOR TOILET TRAINING

RELATED INVENTION

The present invention claims benefit under 35 U.S.C. 119 (e) to "Magic Potty Pouch," U.S. Provisional Patent Application Ser. No. 60/701,699, filed 22 Jul. 2005, which is incorporated by reference herein.

TECHNICAL FIELD OF THE INVENTION

The present invention relates to the field of toilet training. More specifically, the present invention relates to a toilet training kit and a method for encouraging a child in the toilet training process.

BACKGROUND OF THE INVENTION

Toilet training is often a difficult and tedious process for both the child and his or her caregiver. One of the greatest challenges that a caregiver has is to persuade the child to use the toilet when they need to urinate. However, children are sometimes intimidated or simply disinterested in transitioning from diapers to regular toilet use. Forcing an unwilling child to use a toilet can be counterproductive and can reinforce the child's fear or disinterest in the process.

Consequently, there is a need for toilet training aids that make the experience of using the toilet amusing for the child so as to encourage further use of the toilet. A toilet training process that is amusing for the child can make the process easier and consequently more enjoyable for both the child and his or her caregiver. An activity in which the source of amusement to the child is directly related to the activity of urinating in the toilet could have a strong effect in developing a positive incentive in the child's mind for using the toilet.

Positive reinforcement has long been a highly regarded motivational tool in many training endeavors. That is, an offering of desirable effects or consequences for a behavior is provided to increase the probability of that behavior being repeated in the future. In terms of positive reinforcement, a reward should be offered when desirous of motivating a child to use a toilet instead of soiling his or her diaper. Furthermore, that reward must be given to the child after each successful potty experience to reinforce the behavior.

Various systems for facilitating toilet training have been developed. These systems include paper targets, electronic fluid detection systems with audible feedback, compositions that change from white to another color upon wetting by urine, and so forth. Various other teaching tools are available, such as, books, videotapes, charts with stickers, personalized toilets, packages that include a boy or girl doll and a toilet for the doll, and so forth. However, many of these systems are costly, and call for complicated or time consuming setup for the caregiver and/or the management of a multiplicity of parts and pieces.

A known composition is a color additive powder mixed with salt. When urine contacts the composition, the composition dissolves and turns into a non-white color. The intent of the color change of the powder is to provide visual stimulation to the child to encourage him or her to use the toilet. Long-term use of this salt-based composition can be detrimental to plumbing when the urine/salt/color additive mixture is rinsed out of the basin of a child training toilet. In particular, water high in salinity contains significant quantities of total dissolved solids (TDS). Water high in TDS can be harsh on home plumbing systems causing early corrosion of pipes, scaling and spotting, reduced lifespan of appliances, and so forth.

Consequently, a need exists for a toilet training aid and process for facilitating toilet training that enhances the positive experience for the child, is simple to setup and manage for the child's caregiver, and is not harmful to the plumbing.

SUMMARY OF THE INVENTION

Accordingly, it is an advantage of the present invention that a toilet training kit and a method for toilet training are provided.

It is another advantage of the present invention that use of the toilet training kit and associated methodology encourages a child to use the toilet by providing a source of amusement that directly results from the child's use of the toilet.

Another advantage of the present invention is that the toilet training kit and associated methodology employ positive reinforcement techniques for rewarding the child's use of the toilet.

Yet another advantage of the present invention is that the toilet training kit is inexpensive and its contents are simple to setup and manage.

The above and other advantages of the present invention are carried out in one form by a kit for facilitating toilet training. The kit includes a case, a plurality of urine indicators housed in the case that change from a substantially flat profile to an expanded profile upon contact with a liquid, and a learning graphic for recording a progress of the toilet training in response to an expansion of the urine indicators.

The above and other advantages of the present invention are carried out in another form by a method for toilet training a child. The method calls for providing a kit that includes a plurality of packets and a learning graphic, each of the plurality of packets including a mixture of urine indicators and a water soluble color additive powder. The entire content of one of the packets is placed in a dry child training toilet, and the child is positioned in a position appropriate for urination in the toilet. The urine indicators expand and the powder dissolves to change a color of the urine in response to an addition of the urine in the child training toilet. A progress of the urination is recorded on the learning graphic.

BRIEF DESCRIPTION OF THE DRAWINGS

A more complete understanding of the present invention may be derived by referring to the detailed description and claims when considered in connection with the Figures, wherein like reference numbers refer to similar items throughout the Figures, and:

DETAILED DESCRIPTION OF THE PREFERRED EMBODIMENTS

Figure 1:
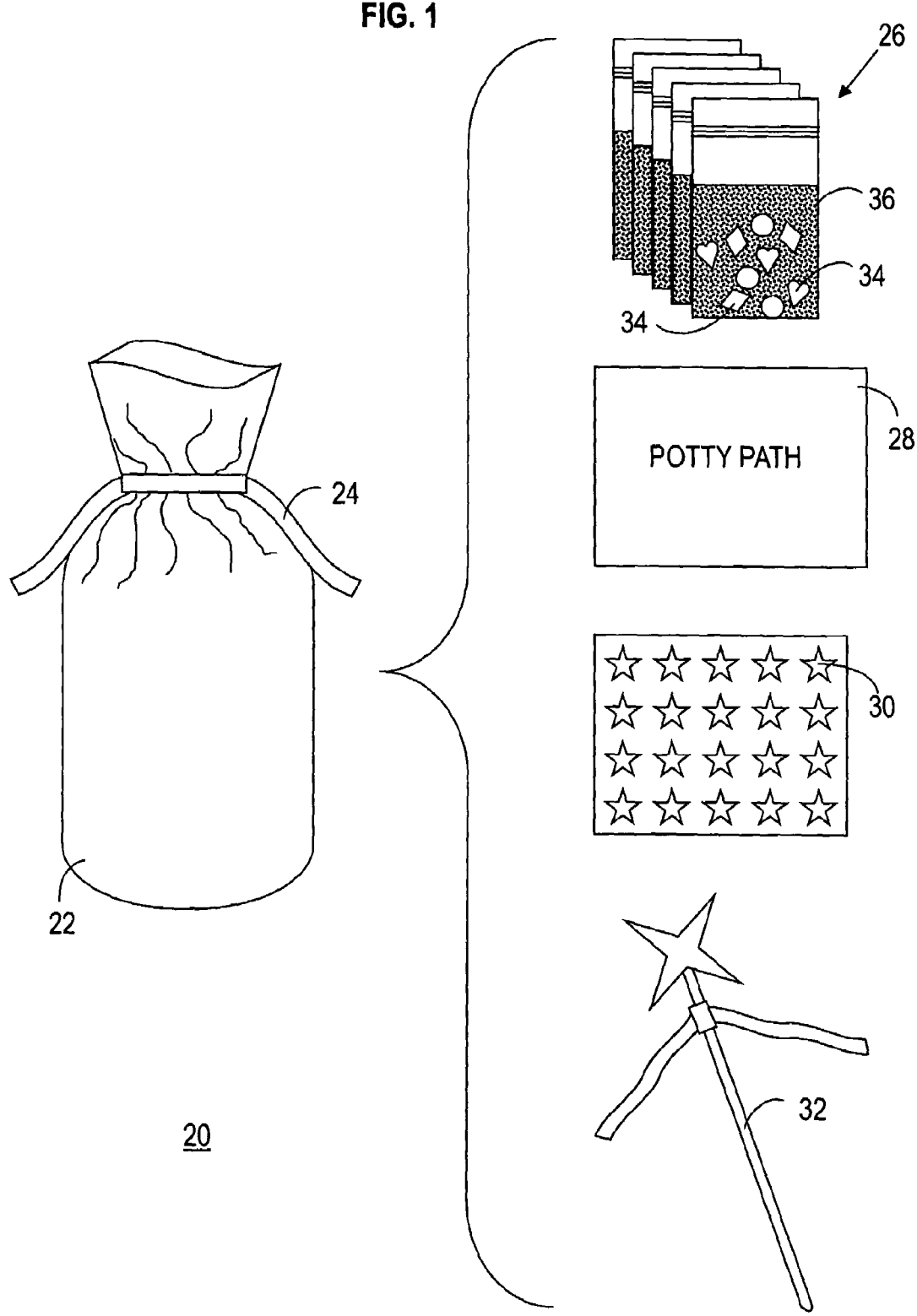
FIG. 1 shows a front view of a toilet training kit and its contents in accordance with a preferred embodiment of the present invention.

FIG. 1 shows a front view of a toilet training kit 20 and its contents in accordance with a preferred embodiment of the present invention. Toilet training kit 20 may be utilized to encourage a child to use the toilet by providing a source of amusement that directly results from the child's use of the toilet.

Toilet training kit 20 includes a case 22 generally in the form of a fabric pouch having a drawstring closure 24. The contents of case 22 include a plurality of packets 26, each containing a single portion of urine indicating material (discussed below), a learning graphic 28, decorative elements 30 in the form of self-adhesive stickers 30, and a prize 32.

In an exemplary embodiment, case 22 may be large enough to house all of packets 26, learning graphic 28, self-adhesive stickers 30, and prize 32 as a single-self contained unit. Case 22 in the form of a fabric pouch may be, for example, golden in color, to enhance its appeal as being magical. Those skilled in the art will recognize, however, that case 22 can take on a number of forms and shapes, and may fabricated from materials that are rigid or semi-rigid.

Each of packets 26 includes a single portion of urine indicating material that includes urine indicators 34 and a liquid indicating powdered mixture 36. Urine indicators 34 are preferably made of substantially white compressed cellulose sponge and are formed into various pre-determined shapes. The compressed cellular sponge material of urine indicators 34 is desirably compressed to approximately ten percent of the expanded thickness of the sponge when wet with a liquid. Contact with the child's urine causes urine indicators 34 to expand from a substantially flat profile to an expanded profile.

Urine indicators 34 can be die-cut from a sheet of compressed cellulose sponge, into a variety of shapes that correspond with a particular theme of kit 20. In this exemplary embodiment, urine indicators 34 are die-cut into hearts, diamonds, circles, and so forth. Those skilled in the art will recognize, however, that urine indicators 34 may be cut into numerous shapes, such as numbers, trucks, cars, stars, superheroes, cartoon characters, and so forth.

Liquid indicating powder mixture 36 is generally a mixture of a sugar with a water-soluble color additive, in powdered or granulated form, uniformly dispersed therein. The sugar is preferably in a finely granulated crystalline or powder form. Sugar is preferred over prior art compositions that utilize salt, because sugar is non-corrosive relative to salt and is thus less harmful to plumbing.

The color additive of mixture 36 is one of a variety of water-soluble color additives that have no known hazardous components. An exemplary water-soluble color additive goes by the trade name "Hot Pink 2880", produced by Robert Koch Industries, Inc., of Bennett, Colo. A relatively small amount of color additive may be mixed with the sugar, for example, one part color additive mixed with one hundred or more parts sugar. When mixed, powder mixture has a generally white appearance due to the relatively small amount of color additive that is present in proportion to the much larger amount of sugar. Contact with the child's urine causes mixture to dissolve into the child's urine. Since the powder mixture is a dye, the child's urine changes from its typical color to a vibrant non-white color. The expansion of urine indicators 34 combined with the color change of the urine responsive to dissolution of mixture 36 provides a visual stimulation to the child to encourage him or her to regularly use the toilet.

Figure 2:
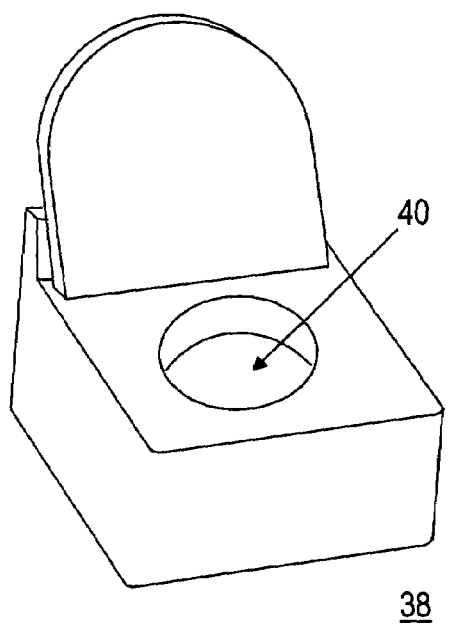
FIG. 2 shows a perspective view of an exemplary child training toilet.

FIG. 2 shows a perspective view of an exemplary child training toilet 38. Prior to a toilet training episode, the entire contents of one of packets 26 (FIG. 1) are placed into a dry urine basin 40 of training toilet 38. The implementation of multiple, single-use packets 26 enables the child's caregiver to easily and rapidly prepare training toilet 38 for use prior to each toilet training episode without the time expenditure needed for measuring out, counting, or otherwise preparing any product for placement into urine basin 40. This rapid preparation is advantageous in child care facilities where multiple children might be using training toilet 38, or when little advance warning of the need to use toilet 38 is given by the child.

As discussed above, urine indicators 34 (FIG. 1) and powder mixture 36 (FIG. 1) are substantially white in color. Consequently, when urine indicators 34 and powder mixture 36 are placed in urine basin 40 they are not readily visible to the child. After the contents of one of packet 26 are placed in urine basin 40, preferably not in view of the child, the child is positioned in a position appropriate for urination in training toilet 38. For most children, the appropriate position is a seated position on training toilet 38. However, for male children, the appropriate position may alternatively be in a standing position near training toilet 38. Once in position, the child is encouraged to urinate.

Should the child urinate, a caregiver could encourage the child in a positive manner to see what happened in toilet 38. Alternatively, the child may discover an event when he or she spontaneously looks into urine basin 40 following urination. Upon urination, urine indicators 34 will rapidly expand and powder mixture 36 will dissolve.

Figure 3:
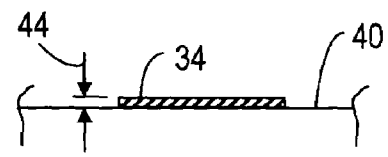
FIG. 3 shows a side view of a dry urine indicator of the present invention.
Figure 4:
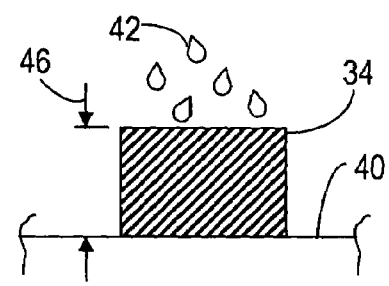
FIG. 4 shows a side view of the urine indicator of FIG. 4 expanded in response to wetting by urine.
Figure 5:
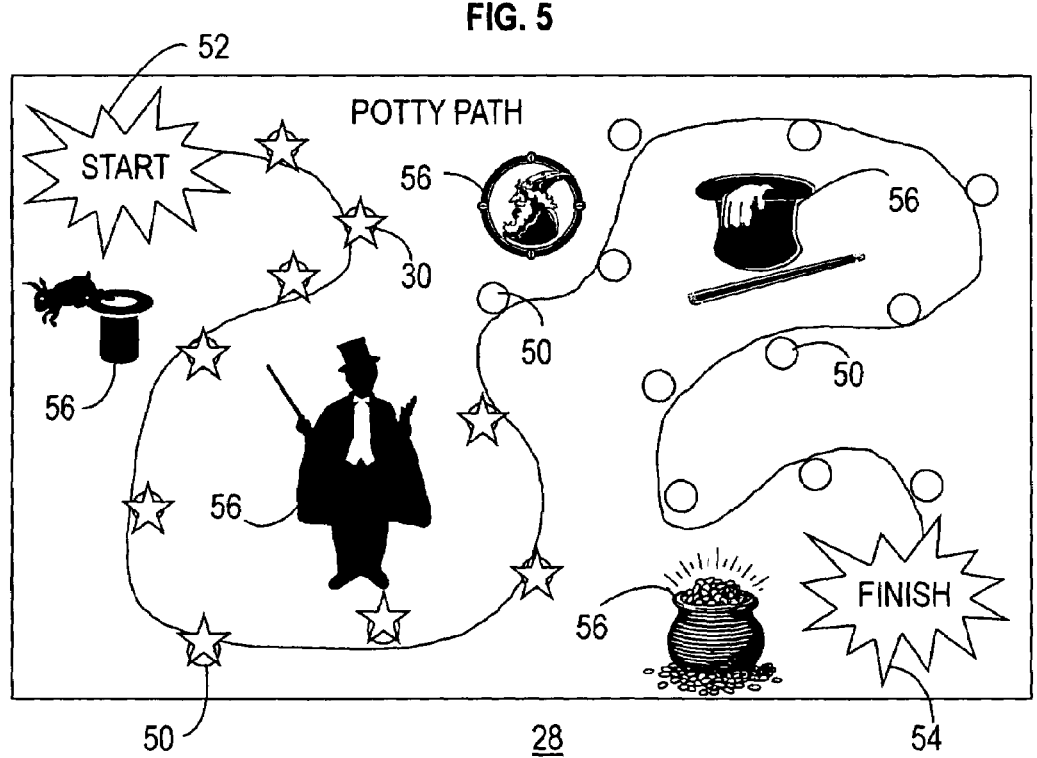
FIG. 5 shows a front view of a learning graphic for recording a progress of the toilet training in accordance with a preferred embodiment of the present invention.

Referring to FIGS. 3-4, FIG. 3 shows a side view of a dry urine indicator 34 lying in urine basin 40, and FIG. 4 shows a side view of urine indicator 34 lying in urine basin 40 and expanded in response to wetting by urine 42. As shown, the dry urine indicator 34 of FIG. 3 exhibits a first thickness 44 that is relatively flat. Following contact with urine 42, urine indicator 34 expands to a second thickness 46 that is approximately ten times that of first thickness 44.

Powder mixture 36 dissolves in the presence of urine 42 and rapidly disperses in and dyes urine 42 a vivid non-white color. In a preferred embodiment, such a color might be hot pink. Due to the rapid dissolution of powder mixture 36, urine indicators 34 can expand drawing in dyed urine 42. Consequently, urine indicators 34 may also take on a vivid non-white hue, causing both the dyed urine 42 and the expanded urine indicators 34 to become highly visible.

The child may experience amusement and surprise upon seeing urine 42 change to a vivid non-white color and upon the sudden appearance of expanded urine indicators 34. After repeated use of packets 26 containing urine indicators 34 and powder mixture 36, it is hoped that the child will develop a positive association between the act of urinating and the amusement of watching his or her urine 42 change color and the sudden visibility of urine indicators 34.

FIG. 6 shows a front view of learning graphic 28 for recording a progress of the toilet training in accordance with a preferred embodiment of the present invention. The motivation of color change and sudden visibility of urine indicators 34 can be positively reinforced through the use of learning graphic 28.

In this exemplary embodiment, learning graphic 28, also called a potty path, is a chart having a progress path 48. Sites in the form of dots 50 are arranged along progress path 48 between a start symbol 52 and a finish symbol 54. Learning graphic 28 may also include images 56 in accordance with a particular theme of toilet training kit 20 (FIG. 1) to make learning graphic 28 more visually appealing to a child. In this exemplary configuration, images 56, such as a top hat, rabbit, magician, wizard, and pot of gold correspond to the aforementioned magical theme.

When a child urinates into training toilet 38 (FIG. 2), the child, with or without a caretaker's help, is encouraged to affix one of stickers 30 onto one of dots 50 beginning at start symbol 52 and progressing to finish symbol 54. Accordingly, the progress of the child's toilet training can be recorded on progress path 48 whenever a child successfully urinates in urine basin 40 (FIG. 2) of training toilet 38, causing urine indicators 34 to expand and powder mixture 36 to dissolve. When each of dots 50 is covered with one of stickers 30, that is, when the child finishes progress path 48, the child can be rewarded with prize 32 (FIG. 1), in this case a wand, housed in case 22 (FIG. 1).

In summary, the present invention teaches of a toilet training kit and a method for toilet training. The toilet training kit includes multiple, single-use packets of urine indicating material. This urine indicating material includes urine indicators that expand in urine and a color changing powder that dissolves in and colors the urine. The sudden color change and appearance of the urine indicators encourages a child to use the toilet by providing a source of amusement that directly results from the child's use of the toilet. In addition, the positive reinforcement technique of recording toilet training progress on a learning graphic by the attachment of decorative elements and the eventual prize rewards the child's use of the toilet. The self-contained case and its contents yield a toilet training kit that is relatively inexpensive, with the single use packets being simple to setup and manage.

Although the preferred embodiments of the invention have been illustrated and described in detail, it will be readily apparent to those skilled in the art that various modifications may be made therein without departing from the spirit of the invention or from the scope of the appended claims. For example, in addition to the color additive, the packet may also contain an effervescing powder and/or a scented powder that rapidly dissolve in the presence of urine to further enhance the toilet training experience.

What is claimed is:

1. A kit for facilitating toilet training comprising:
   a case;
   a plurality of urine indicators housed in said case that change from a substantially flat profile to an expanded profile upon contact with a liquid, said urine indicators being compressed cellulose sponge;
   a water soluble color additive powder housed in said case that dissolves upon contact with said liquid to change a color of said liquid;
   a plurality of packets, each of said plurality of packets including a portion of said urine indicators and a portion of said powder, wherein an entire content of said each packet is placed in a dry child training toilet prior to a toilet training episode; and
   a learning graphic for recording a progress of said toilet training in response to an expansion of said urine indicators.

2. A kit as claimed in claim 1 wherein said case is a pouch having a drawstring closure.

3. A kit as claimed in claim 1 wherein said urine indicators are die-cut from a sheet of said compressed cellulose sponge.

4. A kit as claimed in claim 1 wherein said flat profile of said compressed cellulose sponge exhibits a first thickness, and said expanded profile of said compressed cellulose sponge exhibits a second thickness when wet with said liquid, said second thickness being approximately ten times said first thickness.

5. A kit as claimed in claim 1 wherein said urine indicators are formed into a pre-determined shape.

6. A kit as claimed in claim 1 wherein said urine indicators are of a substantially white color.

7. A kit as claimed in claim 1 wherein said kit further comprises mixture of a sugar with said powder uniformly dispersed therein, said mixture having a substantially white appearance.

8. A kit as claimed in claim 7 wherein said sugar is in a crystalline form.

9. A kit as claimed in claim 1 wherein said learning graphic comprises a progress path, and said kit further comprises decorative elements attachable to said learning graphic along said progress path to indicate said progress of said toilet training.

10. A method for toilet training a child comprising:
    providing a kit that includes a plurality of packets and a learning graphic, each of said plurality of packets including a mixture of urine indicators and a water soluble color additive powder;
    placing an entire content of one of said packets in a dry child training toilet;
    positioning said child in a position appropriate for urination in said toilet, said urine indicators expanding and said powder dissolving to change a color of said urine in response to an addition of urine in said child training toilet; and
    recording a progress of said urination on said learning graphic.

11. A method as claimed in claim 10 wherein said providing comprises providing said urine indicators formed from compressed cellulose sponge in a pre-determined shape and in a substantially white color.

12. A method as claimed in claim 10 wherein said providing comprises providing said powder in a mixture of a sugar with said powder uniformly dispersed therein such that said mixture has a substantially white appearance.

13. A method as claimed in claim 10 further comprising:
    supplying a plurality of decorative elements in said kit; and
    said recording comprises attaching one of said decorative elements on one of a plurality of sites along a progress path of said learning graphic to indicate said progress of said toilet training.

14. A method as claimed in claim 13 further comprising:
    supplying a prize in said kit; and
    repeating said placing, positioning, and recording operations; and
    rewarding said child with said prize when each of said plurality of sites has said one of said decorative elements attached thereto.

15. A kit for facilitating toilet training comprising:
    a case;
    a plurality of urine indicators housed in said case, said urine indicators being formed from compressed cellulose sponge having a substantially white color, and said urine indicators changing from a substantially flat profile to an expanded profile upon contact with a liquid;
    a mixture of a sugar and a water soluble color additive powder uniformly dispersed in said sugar, said mixture having a substantially white appearance and lacking a salt, said sugar being in a crystalline form, and said powder dissolving upon contact with said liquid to change a color of said liquid; and
    a learning graphic for recording a progress of said toilet training in response to an expansion of a portion of said urine indicators.

* * * * *